United States Patent
Grimsby et al.

(10) Patent No.: US 12,083,216 B2
(45) Date of Patent: Sep. 10, 2024

(54) HEMOSTATIC COMPOSITIONS AND RELATED METHODS

(71) Applicant: Boston Scientific Scimed, Inc., Maple Grove, MA (US)

(72) Inventors: Jessica L. Grimsby, Watertown, MA (US); Lauren Lydecker, Millbury, MA (US); Gerald Fredrickson, Westford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/177,894

(22) Filed: Feb. 17, 2021

(65) Prior Publication Data

US 2021/0251890 A1    Aug. 19, 2021

Related U.S. Application Data (60) Provisional application No. 62/977,989, filed on Feb. 18, 2020.

(51) Int. Cl.
| | |
|---|---|
| *A61K 9/00* | (2006.01) |
| *A61K 9/14* | (2006.01) |
| *A61K 31/722* | (2006.01) |
| *A61K 45/06* | (2006.01) |
| *A61K 47/02* | (2006.01) |

(52) U.S. Cl.
CPC .............. *A61K 9/0024* (2013.01); *A61K 9/14* (2013.01); *A61K 31/722* (2013.01); *A61K 45/06* (2013.01); *A61K 47/02* (2013.01)

(58) Field of Classification Search
CPC .................................................. A61K 31/722
See application file for complete search history.

(56) References Cited

U.S. PATENT DOCUMENTS

| | | |
|---|---|---|
| 471,854 A | 3/1892 | Howard |
| 881,238 A | 3/1908 | Hasbrouck |
| 1,145,520 A | 7/1915 | Smith |
| 1,599,959 A | 9/1926 | Buheiji |
| 1,732,566 A | 10/1929 | McKendrick |
| 2,151,418 A | 3/1939 | Bolté |
| 2,185,927 A | 6/1940 | Shelanski |
| 2,478,715 A | 8/1949 | Schmitt |
| 2,623,519 A | 12/1952 | Cohen |
| 3,669,113 A | 6/1972 | Altounyan et al. |
| 3,940,061 A | 2/1976 | Gimple et al. |
| 4,184,258 A | 6/1980 | Barrington et al. |
| 4,427,450 A | 1/1984 | Kostansek |
| 4,457,329 A | 7/1984 | Werley et al. |
| 4,806,167 A | 2/1989 | Raythatha |
| 5,215,221 A | 6/1993 | Dirksing |
| 5,231,983 A | 8/1993 | Matson et al. |
| 5,273,531 A | 12/1993 | Knoepfler |
| 5,312,331 A | 5/1994 | Kneopfler |
| 5,312,333 A | 5/1994 | Churinetz et al. |
| 5,366,122 A | 11/1994 | Guentert et al. |
| 5,445,612 A | 8/1995 | Terakura et al. |
| 5,470,311 A | 11/1995 | Setterstrom et al. |
| 5,884,621 A | 3/1999 | Matsugi et al. |
| 5,951,531 A | 9/1999 | Ferdman et al. |
| 6,003,512 A | 12/1999 | Gerde |
| 6,484,750 B1 | 11/2002 | Foos et al. |
| 6,554,022 B2 | 4/2003 | Wakeman |
| 6,589,087 B2 | 7/2003 | Mackal et al. |
| 6,684,917 B2 | 2/2004 | Zhu et al. |
| 6,708,712 B2 | 3/2004 | Wakeman |
| 6,716,190 B1 | 4/2004 | Glines et al. |
| 6,799,571 B1 | 10/2004 | Hughes et al. |
| 7,178,547 B2 | 2/2007 | Mackal |
| 7,311,270 B2 | 12/2007 | Kapila |
| 7,334,598 B1 | 2/2008 | Hollars |
| 7,361,300 B2 | 4/2008 | Kelly et al. |
| 7,427,607 B2 | 9/2008 | Suzuki |
| 7,455,248 B2 | 11/2008 | Kablik et al. |
| 7,461,649 B2 | 12/2008 | Gamard et al. |
| 7,544,177 B2 | 6/2009 | Gertner |
| 7,563,299 B2 | 7/2009 | Baptista da Costa et al. |
| 7,673,647 B2 | 3/2010 | Mackal |
| 7,841,338 B2 | 11/2010 | Dunne et al. |
| 7,892,205 B2 | 2/2011 | Palasis et al. |
| 7,921,874 B2 | 4/2011 | Tekulve et al. |

(Continued)

FOREIGN PATENT DOCUMENTS

| | | |
|---|---|---|
| CN | 101401956 B | 11/2012 |
| CN | 104162183 A | 11/2014 |

(Continued)

OTHER PUBLICATIONS

Aiyuan, Journal of Medical Collages of PLA, 26, 2011 (Year: 2011).*
Crowell et al., "Effect of Acidity on Blood Coagulation," American Physiological Society, pp. 379-381 (1961).
Green et al., "Effect of Acid and Pepsin on Blood Coagulation and Platelet Aggregation," Gastroenterology, vol. 74, pp. 38-43 (1978).
Patchett, et al. "Clot Lysis by Gastric Juice: an in Vitro Study," Gut, vol. 30, pp. 1704-1707 (1989).
Satishbabu et al., "Formulation and Evaluation of Floating Drug Delivery System of Famotidine," Indian J. Pharm Sci, vol. 72, No. 6, pp. 738-744 (2010).
Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — Susan T Tran
*Assistant Examiner* — William Craigo
(74) *Attorney, Agent, or Firm* — Bookoff McAndrews, PLLC (57) ABSTRACT

Compositions and related kits and methods for treating a target site of a patient are described herein. The composition may include a hemostatic agent and a pH agent, for example. Methods of treatment include delivering and applying the hemostatic agent and the pH agent to a gastrointestinal system of a patient via a medical device to reduce bleeding of tissue in the gastrointestinal system.

16 Claims, 3 Drawing Sheets

(56) References Cited

U.S. PATENT DOCUMENTS

| | | | |
|---|---|---|---|
| 8,037,880 B2 | 10/2011 | Zhu et al. |
| 8,097,071 B2 | 1/2012 | Burgess et al. |
| 8,118,777 B2 | 2/2012 | Ducharme et al. |
| 8,269,058 B2 | 9/2012 | McCarthy et al. |
| 8,313,474 B2 | 11/2012 | Campbell et al. |
| 8,360,276 B2 | 1/2013 | Rogier et al. |
| 8,361,054 B2 | 1/2013 | Ducharme et al. |
| 8,496,189 B2 | 7/2013 | Lomond et al. |
| 8,673,065 B2 | 3/2014 | Burgess et al. |
| 8,721,582 B2 | 5/2014 | Ji |
| 8,728,032 B2 | 5/2014 | Ducharme et al. |
| 8,741,335 B2 | 6/2014 | McCarthy |
| 8,827,980 B2 | 9/2014 | Ji |
| 8,910,627 B2 | 12/2014 | Iwatschenko et al. |
| 8,951,565 B2 | 2/2015 | McCarthy |
| 9,028,437 B2 | 5/2015 | Ott et al. |
| 9,089,658 B2 | 7/2015 | Dunne et al. |
| 9,101,744 B2 | 8/2015 | Ducharme |
| 9,107,668 B2 | 8/2015 | Melsheimer et al. |
| 9,132,206 B2 | 9/2015 | McCarthy |
| 9,204,957 B2 | 12/2015 | Gregory et al. |
| 9,205,170 B2 | 12/2015 | Lucchesi et al. |
| 9,205,207 B2 | 12/2015 | Ji |
| 9,205,240 B2 | 12/2015 | Greenhalgh et al. |
| 9,308,584 B2 | 4/2016 | Burgess et al. |
| 9,310,812 B2 | 4/2016 | Costle et al. |
| 9,375,533 B2 | 6/2016 | Ducharme et al. |
| 9,492,646 B2 | 11/2016 | Hoogenakker et al. |
| 9,517,976 B2 | 12/2016 | Mackal |
| 9,545,490 B2 | 1/2017 | Iwatschenko et al. |
| 9,555,185 B2 | 1/2017 | Foster et al. |
| 9,629,966 B2 | 4/2017 | Ji |
| 9,636,470 B2 | 5/2017 | Pohlmann et al. |
| 9,707,359 B2 | 7/2017 | Kubo |
| 9,713,682 B2 | 7/2017 | Eistetter et al. |
| 9,717,897 B2 | 8/2017 | Rogier |
| 9,821,084 B2 | 11/2017 | Diegelmann et al. |
| 9,839,772 B2 | 12/2017 | Ducharme |
| 9,839,774 B2 | 12/2017 | Bonaldo |
| 9,846,439 B2 | 12/2017 | Carman et al. |
| 9,867,931 B2 | 1/2018 | Gittard |
| 9,976,660 B2 | 5/2018 | Stanton et al. |
| 10,004,690 B2 | 6/2018 | Lee et al. |
| 10,010,705 B2 | 7/2018 | Greenhalgh et al. |
| 10,017,231 B2 | 7/2018 | Fawcett, Jr. |
| 10,036,617 B2 | 7/2018 | Mackal |
| 10,065,004 B2 | 9/2018 | Eder et al. |
| 10,173,019 B2 | 1/2019 | Kaufmann et al. |
| 10,384,049 B2 | 8/2019 | Stanton et al. |
| 10,420,794 B2 | 9/2019 | Medina et al. |
| 10,463,811 B2 | 11/2019 | Lee et al. |
| 10,507,293 B2 | 12/2019 | Goodman et al. |
| 10,646,706 B2 | 5/2020 | Rogier |
| 10,730,595 B2 | 8/2020 | Fawcett |
| 10,751,523 B2 | 8/2020 | Rogier |
| 10,806,853 B2 | 10/2020 | Gittard |
| 10,850,814 B2 | 12/2020 | Fawcett |
| 10,994,818 B2 | 5/2021 | Hernandez |
| 2004/0107963 A1 | 6/2004 | Finlay et al. |
| 2004/0249359 A1 | 12/2004 | Palasis et al. |
| 2005/0121025 A1 | 6/2005 | Gamard et al. |
| 2005/0147656 A1 | 7/2005 | McCarthy et al. |
| 2005/0220721 A1 | 10/2005 | Kablik et al. |
| 2005/0284809 A1 | 12/2005 | Looney et al. |
| 2006/0004314 A1 | 1/2006 | McCarthy et al. |
| 2006/0213514 A1 | 9/2006 | Price et al. |
| 2007/0056586 A1 | 3/2007 | Price et al. |
| 2007/0066920 A1 | 3/2007 | Hopman et al. |
| 2007/0066924 A1 | 3/2007 | Hopman et al. |
| 2007/0082023 A1 | 4/2007 | Hopman et al. |
| 2007/0125375 A1 | 6/2007 | Finlay et al. |
| 2007/0151560 A1 | 7/2007 | Price et al. |
| 2007/0083137 A1 | 8/2007 | Hopman et al. |
| 2007/0199824 A1 | 8/2007 | Hoerr et al. |
| 2007/0237811 A1 | 10/2007 | Scherr |
| 2008/0021374 A1 | 1/2008 | Kawata |
| 2008/0287907 A1 | 11/2008 | Gregory et al. |
| 2009/0101144 A1 | 4/2009 | Gamard et al. |
| 2009/0155342 A1 | 6/2009 | Diegemann et al. |
| 2009/0281486 A1 | 11/2009 | Ducharme |
| 2010/0121261 A1 | 5/2010 | Kablik et al. |
| 2010/0305505 A1 | 12/2010 | Ducharme et al. |
| 2011/0073200 A1 | 3/2011 | Overvaag et al. |
| 2011/0274726 A1 | 11/2011 | Guo et al. |
| 2011/0308516 A1 | 12/2011 | Price et al. |
| 2014/0271491 A1 | 9/2014 | Gittard et al. |
| 2014/0356433 A1* | 12/2014 | Shieh ............... A61K 31/4439 514/777 |
| 2015/0094649 A1 | 4/2015 | Gittard |
| 2015/0125513 A1 | 5/2015 | McCarthy |
| 2016/0074602 A1* | 3/2016 | Wang ............... A61M 15/0003 604/518 |
| 2016/0375202 A1 | 12/2016 | Goodman et al. |
| 2017/0106181 A1 | 4/2017 | Bonaldo et al. |
| 2017/0232141 A1* | 8/2017 | Surti ............... A61F 13/00063 602/61 |
| 2017/0252479 A1 | 9/2017 | Ji et al. |
| 2017/0296760 A1 | 10/2017 | Lee et al. |
| 2018/0099088 A1 | 4/2018 | Gittard |
| 2018/0193574 A1 | 7/2018 | Smith et al. |
| 2018/0214160 A1 | 8/2018 | Hoskins et al. |
| 2018/0339144 A1 | 11/2018 | Greenhalgh et al. |
| 2019/0134366 A1 | 5/2019 | Erez et al. |
| 2019/0217315 A1 | 7/2019 | Maguire et al. |
| 2019/0232030 A1 | 8/2019 | Pic et al. |
| 2021/0024187 A1 | 1/2021 | Fawcett et al. |
| 2021/0069485 A1 | 3/2021 | Rogier |

FOREIGN PATENT DOCUMENTS

| | | | |
|---|---|---|---|
| DE | 60215438 T2 | 8/2007 | |
| EP | 3052168 B1 | 11/2019 | |
| JP | H07118305 A | 5/1995 | |
| WO | 03013552 A1 | 2/2003 | |
| WO | 2004066806 A2 | 8/2004 | |
| WO | 2005062896 A2 | 7/2005 | |
| WO | WO-2006049463 A1 * | 5/2006 | ............. A61K 31/74 |
| WO | 2006071649 A2 | 7/2006 | |
| WO | 2006088912 A2 | 8/2006 | |
| WO | 2008033462 A2 | 3/2008 | |
| WO | 2009061409 A1 | 5/2009 | |
| WO | 2015050814 A1 | 4/2015 | |
| WO | 2018157772 A1 | 9/2018 | |
| WO | WO-2018184021 A1 * | 10/2018 | ............. A61J 1/2096 |
| WO | WO-2019133894 A1 * | 7/2019 | ........ A61B 17/00234 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

(56) References Cited

OTHER PUBLICATIONS

Aslanian, Harry R., and Loren Laine. "Hemostatic powder spray for GI bleeding." Gastrointestinal endoscopy 77.3 (2013): 508-510.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.
Retsch GmbH Haan. Sieve Analysis: Taking a Close Look at Quality, An Expert Guide to Particle Size Analysis. 2015. (56 pages, in English).
Micromeritics. Density Analysis, 2001. (6 pages, in English).
Micromeritics. "Application Note: Bulk and Skeletal Density Computations for the AutoPore." May 2012. (3 pages, in English).
Arefnia, Ali, et al. "Comparative Study on the Effect of Tire-Derived Aggregate on Specific Gravity of Kaolin." Electronic Journal of Geotechnical Engineering 18 (2013): 335-44.
Kesavan, Jana, et al. "Density Measurements of Materials Used in Aerosol Studies". Edgewoodbiological Center Aberdeen Proving Ground MD, 2000.
International Search Report issued in PCT/US2021/018353, mailed Jul. 16, 2021 (6 pages).

\* cited by examiner

HEMOSTATIC COMPOSITIONS AND RELATED METHODS

CROSS-REFERENCE TO RELATED APPLICATIONS

This application claims the benefit of priority from U.S. Provisional Application No. 62/977,989, filed on Feb. 18, 2020, which is incorporated by reference herein in its entirety.

TECHNICAL FIELD

The present disclosure relates generally to therapeutic materials and related methods of preparation and treatment. For example, the present disclosure includes hemostatic materials useful for treating tissue.

BACKGROUND

Hemorrhages, i.e., bleeding, of internal and external wounds cause numerous medical concerns, including blood loss and risk of infection. Various medical procedures may cause temporary or sustained bleeding. Gastrointestinal hemorrhages, unlike external wounds, may exhibit oozing and rebleeding that can last hours to days, which may result in massive blood loss and patient death. For example, endoscopic procedures performed within the gastrointestinal tract or other organs may result in a wound, or a patient may suffer from a condition that includes gastrointestinal bleeding. Medical devices such as clips can be used to treat internal bleeding, but could inadvertently cause additional tissue damage or may not be sufficiently sized for larger wounds. Bioresorbable materials suffer additional drawbacks in an inability to withstand the hostile environment of the stomach, which inhibits hemostasis and coagulation.

SUMMARY OF THE DISCLOSURE

The present disclosure includes therapeutic materials and methods of preparation and treatment thereof. For example, the present disclosure includes a composition comprising at least one hemostatic agent and at least one pH agent, wherein a weight ratio of the hemostatic agent to the pH agent (hemostatic agent:pH agent) ranges from 10:1 to 1:10. In some examples herein, the hemostatic agent comprises chitosan. For example, the hemostatic agent may comprise a chitosan salt such as chitosan acetate, chitosan succinate, chitosan glutamate, chitosan glycolate, chitosan citrate, or a combination thereof, and/or chitosan cross-linked with tripolyphosphate. The pH agent may comprise, for example, sodium bicarbonate, aluminum hydroxide, calcium hydroxide, magnesium hydroxide, bismuth subsalicylate, or a combination thereof. According to some aspects of the present disclosure, the composition is in the form of a powder, a solution, or a suspension. The average particle diameter of the hemostatic agent may be about 100 µm to about 750 µm, such as about 200 µm to about 550 µm, or about 400 µm to about 550 µm. In some examples, the composition comprises about 10% to about 90% by weight of the at least one hemostatic agent, with respect to the total weight of the composition. Additionally, or alternatively, the composition may comprise about 5 g to about 35 g of the hemostatic agent.

The present disclosure includes a kit comprising the composition as described above, along with a pharmaceutical agent or therapeutic agent. In some examples, the composition is a first composition and the kit further comprises a second composition that comprises a biocompatible monomer or polymer, or a pharmaceutical agent or a therapeutic agent. According to some aspects of the present disclosure, the pharmaceutical agent comprises a histamine-2 blocker such as famotidine.

Also disclosed herein are medical devices comprising a composition and/or a kit described above or elsewhere herein. The present disclosure also includes use of the composition and/or the kit to treat gastrointestinal bleeding. For example, the composition may be formulated as a powder for application to gastrointestinal tissue in an endoscopic procedure.

The present disclosure also includes a method of treating a patient, the method comprising introducing a medical device into a gastrointestinal system of a patient; applying at least one hemostatic agent to a target site of the patient with the medical device, wherein the target site includes bleeding stomach tissue; and increasing a pH of the target site by applying at least one pH agent to the target site; wherein the at least one hemostatic agent reduces bleeding of the stomach tissue. The pH agent(s) may be applied within 30 seconds of applying the at least one hemostatic agent. In some examples, the pH agent comprises sodium bicarbonate, aluminum hydroxide, calcium hydroxide, magnesium hydroxide, bismuth subsalicylate, or a combination thereof. The method may include the hemostatic agent and the pH agent being applied to the target site simultaneously; the pH agent being applied from 1 second to 30 seconds after applying the hemostatic agent; and/or the hemostatic agent being applied as a composition that also comprises the at least one pH agent, and the at least one pH agent being applied from 1 second to 30 seconds after applying the composition. In some examples, the hemostatic agent comprises chitosan. For example, the hemostatic agent may comprise a chitosan salt, chitosan cross-linked with tripolyphosphate, or a mixture thereof. The hemostatic agent may be applied in particle form. In some examples, the hemostatic agent and the pH agent are each applied in particle form. In some examples, the pH agent is applied as a solution, a suspension, or in particle form. The method may further include applying a therapeutic agent or a pharmaceutical agent after applying the at least one hemostatic agent and the at least one pH agent. For example, the method may include applying a pharmaceutical agent that comprises a histamine-2 blocker.

Also provided herein is a method of treating a patient, the method comprising applying a composition to a target site of a gastrointestinal system of the patient, the composition comprising a chitosan salt chitosan cross-linked with tripolyphosphate, or a mixture thereof; and at least one pH agent chosen from sodium bicarbonate, aluminum hydroxide, calcium hydroxide, magnesium hydroxide, bismuth subsalicylate, and combinations thereof; wherein the target site includes bleeding stomach tissue; and wherein the composition reduces bleeding of the stomach tissue. In some examples, the weight ratio of the hemostatic agent to the pH agent (hemostatic agent:pH agent) ranges from 10:1 to 1:10. In some examples, the composition is a first composition, and the method further comprise applying a second composition to the target site after applying the first composition, the second composition comprising at least one pH agent that is the same or different than the at least one pH agent of the first composition. The second composition may further comprise a therapeutic agent or a pharmaceutical agent, e.g., a histamine-2 blocker. The second composition may be applied, e.g., from 1 second to 30 seconds after applying the first composition.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Aspects of the present disclosure are described in greater detail below. The terms and definitions provided herein control, if in conflict with terms and/or definitions incorporated by reference.

As used herein, the terms "comprises," "comprising," or any other variation thereof are intended to cover a non-exclusive inclusion, such that a process, method, composition, article, or apparatus that comprises a list of elements does not include only those elements, but may include other elements not expressly listed or inherent to such process, method, composition, article, or apparatus. The term "exemplary" is used in the sense of "example" rather than "ideal."

As used herein, the singular forms "a," "an," and "the" include plural reference unless the context dictates otherwise. The terms "approximately" and "about" refer to being nearly the same as a referenced number or value. As used herein, the terms "approximately" and "about" should be understood to encompass ±5% of a specified amount or value.

Embodiments of the present disclosure include materials, e.g., therapeutic agents, and related methods of treatment for tissues. The methods herein include endoscopic delivery of materials to provide for hemostasis of tissue, e.g., as part of a hemostatic system. The hemostatic systems herein may comprise one or more compounds, including one or more biomaterials that are biocompatible and/or derived from biological materials, wherein the compound(s) may be at least partially or completely bioresorbable. For example, upon application to tissue, at least a portion of the material(s) may dissolve and/or be absorbed by the body over time. In some cases, a portion of the material(s) may be shed from the site of application to be absorbed and/or removed from the body via the gastrointestinal system. Although embodiments of the present disclosure may be described with specific reference to systems and methods directed to treatment of gastrointestinal tissue, it is understood that any treatment site in a patient may be targeted by the exemplary systems and methods disclosed herein.

The materials herein may be used to treat various types of tissues, including wounded and/or diseased tissue. For example, the materials may be useful for treating gastrointestinal bleeding associated with various conditions and/or following a medical procedure. The tissue to be treated may include, for example, burns, lacerations, lesions, inflammation, ulceration, perforations, microperforations, and other types of tissue in need of treatment or repair. The materials herein may be used as an alternative to, or in combination with, adhesive and/or medical devices such as sutures or staples, and/or other devices or methods for securing or protecting tissue. In at least one example, the material(s) may be applied to inhibit, stop, or prevent bleeding of tissue at a target site.

Exemplary sites to which the systems herein may be applied include, but are not limited to, tissues of the gastrointestinal system such as, e.g., the esophagus, the stomach, the small intestine (e.g., duodenum, jejunum, and/or ileum), and/or the large intestine (e.g., cecum, colon, rectum, and/or anal canal). The materials herein may be applied to damaged tissue resulting from disease or injury, and/or may be applied to tissue following a medical procedure.

Gastrointestinal bleeding can occur in the upper gastrointestinal tract, which includes, e.g., the esophagus, the stomach, and the small intestine. The stomach provides a challenging environment to stop bleeding due to its relatively low pH, e.g., generally ranging from about 1.5 to about 3.5. This low, acidic, pH can promote enzymatic activities (e.g., pepsin protease, which generally functions at a low pH during digestion to degrade proteins), while hindering protein-dependent biochemical processes involved in hemostasis. Such biochemical processes include, e.g., platelet aggregation, blood coagulation, and stability of platelet plugs and formed fibrin clots.

The acidic environment of the stomach may impair clot formation as well as increase clot degradation via fibrinolysis. For example, the low pH of the gastrointestinal system, including the stomach, may impact acute hemostasis and inhibit initial coagulation processes that form a platelet plug and fibrin clot at a bleeding tissue site. Further, since fibrin clots are more susceptible to degradation and/or rupture in an acidic, proteolytic environment, low pH inhibits sustained hemostasis after the initial fibrin clot has already formed. The compositions and materials thereof herein may be formulated to address the low pH environment of the gastrointestinal system when applied endoscopically to treat tissue. For example, the materials herein may be useful to reduce, inhibit, stop, and/or prevent bleeding at a target site while counteracting the low pH environment of the gastrointestinal system, e.g., the stomach, to promote initial clot formation and sustained hemostasis. The compositions herein may comprise one or more hemostatic agents without pH agents, one or more pH agents without hemostatic agents, or at least one hemostatic agent in combination with at least one pH agent. The compositions herein may be applied to a target site, e.g., bleeding tissue, in any order. Without being bound by theory, it is believed that applying one or more hemostatic agents and one or more pH agents simultaneously or in close sequence may provide a synergistic effect to promote acute hemostasis in a low pH environment.

The systems herein may comprise one or more materials that serve as hemostatic agent(s). The hemostatic agent(s) may be natural or derived from natural materials, or may be at least partially synthetic in origin. For example, the hemostatic agent(s) may comprise one or more polysaccharides (e.g., chitosan, natural gums, alginate), including cellulose, starch (e.g., potato or other plant starch), and/or glycogen. In at least one example, the hemostatic agent(s) may be charged, e.g., cationic.

In some examples herein, the hemostatic agent(s) may comprise chitosan, optionally in combination with one or more other hemostatic agents. Chitosan is a linear polysaccharide formed of glucosamine units derived from chitin, the structural component of crustacean exoskeletons:

Chitosan is typically prepared by deacetylation of chitin with an alkaline reagent such as sodium hydroxide, yielding a water-soluble material. Chitosan is antimicrobial and cationic with natural bioadhesive properties that allow it to bind to negatively charged surfaces such as mucosal membranes and concentrate blood components, e.g., red blood cells, to promote coagulation. For example, chitosan materials may absorb water from blood plasma and concentrate blood components, e.g., red blood cells, platelets, and blood proteins, to form an initial non-fibrin clot, generally referred to herein as a pseudoclot.

The hemostatic systems herein may comprise chitosan in the form of a biocompatible salt. For example, salts may be prepared by combining chitosan with a suitable conjugate acid such as acetic acid (forming chitosan acetate) or lactic acid (forming chitosan lactate). Other possible organic acids include, but are not limited to, succinic acid (chitosan succinate), glutamic acid (chitosan glutamate), glycolic acid (chitosan glycolate), and citric acid (chitosan citrate). In some examples, the hemostatic agent(s) may comprise chitosan acetate. Additionally or alternatively, the hemostatic systems herein may comprise chitosan cross-linked with another material, such as tripolyphosphate (TPP). For example, chitosan cross-linked with TPP may be prepared by combining chitosan with sodium TPP. Without being bound by theory, it is believed that using chitosan cross-linked with TPP may have benefits in a low pH environment like the stomach or other portions of the gastrointestinal system as compared to other hemostatic agents like salts. Chitosan salts generally have a somewhat acidic pH when combined with a physiological medium like saline solution or phosphate-buffered saline (PBS). As an example, chitosan acetate may have a pH of less than 6, e.g., from 3 to 6, from 4 to 5.5, or from 5 to 6 when added to saline solution or PBS, e.g., in view of dissociation of the acetate ion from the salt. By comparison, chitosan cross-linked with TPP generally has a higher pH when added to the same physiological medium, e.g., a more neutral or somewhat basic pH, such as pH greater than or equal to 7, e.g., from 7 to 12, from 7 to 8, from 7.4 to 10, or from 7.6 to 9, when added to saline solution or PBS. Accordingly, applying chitosan cross-linked with TPP to tissue as a hemostatic agent in acidic environments may provide a localized neutralizing effect to the tissue.

In some examples, the hemostatic agent(s) may be in particle form, e.g., formulated as a powder, or may be liquid form, e.g., formulated as a spray such as with a biocompatible liquid. When in particle form, the hemostatic agent(s) may have a particle size to facilitate administration to an internal bleeding site, e.g., via a suitable medical device for endoscopic delivery. According to some examples herein, the particles of the hemostatic agent(s) may have an average particle diameter of about 100 μm to about 750 μm, such as about 100 μm to about 500 μm, about 150 μm to about 550 μm, about 200 μm to about 550 μm, about 200 μm to about 450 μm, about 300 μm to about 450 μm, about 400 μm to about 550 μm, about 450 μm to about 650 μm, or about 500 μm to about 600 μm. When in liquid form, the hemostatic agent(s) may be dissolved or suspended in a biocompatible liquid, such as water or an aqueous solution (e.g., saline solution) or an alcohol, among other examples.

The materials and hemostatic systems herein may comprise one or more hemostatic agents in combination with one or more pH agents, wherein the pH agents may assist in counteracting the acidity of the gastrointestinal tract, e.g., the stomach. When chitosan cross-linked with TPP is used as a hemostatic agent, both the hemostatic agent and the pH agent(s) may provide a localized neutralizing effect to tissue in an acidic environment. Exemplary pH agents include, but are not limited to, sodium bicarbonate, aluminum (e.g., aluminum hydroxide), calcium (e.g., calcium carbonate), magnesium (e.g., magnesium hydroxide), bismuth subsalicylate, and combinations thereof. The pH agent(s) may be in particle form, e.g., formulated as a powder, or may be liquid form, e.g., formulated as a spray such as with a biocompatible liquid. In some examples, the pH agent(s) may comprise sodium bicarbonate. When in particle form, the pH agent(s) may have a particle size to facilitate administration to a bleeding site, e.g., by a suitable medical device for endoscopic delivery. The particles of the pH agent may have the same or different average particle diameter as the hemostatic agent(s). In some examples herein, the hemostatic agent(s) and pH agent(s) may have the same or similar particle size, e.g., to facilitate delivery through a suitable medical device.

As mentioned above, the compositions herein may be applied to a target site in any desired order. In some examples, the at least one hemostatic agent may be applied to tissue before, after, or at the same time as at least one pH agent. For example, the hemostatic agent(s) and the pH agent(s) optionally may be combined to form a composition in the form of a hemostatic mixture. Combining the hemostatic agent(s) and the pH agent(s) prior to application to tissue may facilitate treatment in some cases. In some examples, the hemostatic agent(s) may be applied to tissue first, followed by application of one or more other hemostatic agent(s) and/or pH agent(s), optionally in the form of a hemostatic mixture. In some examples, the pH agent(s) may be applied to tissue first, followed by application of one or more other pH agent(s) and/or hemostatic agent(s), optionally in the form of a hemostatic mixture.

Each of the hemostatic agent(s) and the pH agent(s) may be applied in suitable amounts to therapeutically treat the target tissue. The amount of hemostatic agent(s) may be determined based on the nature of the target site, e.g., the extent of the hemorrhage and/or the size of the target site, and the type(s) of hemostatic agent(s) (including any neutralizing capability provided by chitosan cross-linked with TPP as mentioned above). Similarly, the amount of pH agent(s) may be determined based on the pH at and around the target site (including the amount of pH agent(s) and/or the amount of hemostatic agent in the case of chitosan cross-linked with TPP needed to provide for a neutral or near neutral pH at and around the target site), the nature of the target site, and the type(s) and amount of hemostatic agent(s) applied. According to some aspects herein, the amount of hemostatic agent(s) applied to a target site may range from about 1 g to about 50 g, e.g., about 5 g to about 35 g, about 10 g to about 20 g, about 8 g to about 15 g, about 1 g to about 10 g, about 25 g to about 45 g, about 30 g to about 40 g, or about 15 g to about 20 g.

In the case of a mixture, the hemostatic agent(s) may be present in an amount of about 10% to about 99% by weight, relative to the total weight of the mixture. For example, the hemostatic agent(s) (that is, the total amount of hemostatic agents) may be present in an amount of about 20% to about 99%, about 30% to about 99%, about 40% to about 99%, about 50% to about 99%, about 60% to about 99%, about 70% to about 99%, or about 80% to about 99%, all by weight, relative to the total weight of the mixture. Further, for example, the pH agent(s) may be present in an amount of about 1% to about 90% by weight, relative to the total weight of the mixture. For example, the pH agent(s) (that is, the total amount of pH agents) may be present in an amount of about 10% to about 90%, about 10% to about 80%, about 10% to about 70%, about 10% to about 60%, about 10% to about 50%, about 10% to about 40%, about 10% to about 30%, or about 10% to about 20%, all by weight, relative to the total weight of the mixture.

Exemplary methods of treatment using the materials herein will be described below with reference to FIGS. 1A-1C, 2A-2C, and 3A-3E. The figures illustrate exemplary methods of delivering compositions that comprise hemostatic agents to a bleeding tissue surface 100 of a patient. For example, the tissue 100 may be present in a patient's gastrointestinal system, such as tissue of the esophagus, the stomach, or the small intestine. The tissue 100 includes a target site 110 such as a cut, laceration, or other wound. For example, target site 110 may result from torn or cut tissue, e.g., due to an injury or as part of a medical procedure, such as a biopsy.

Figure 1A:
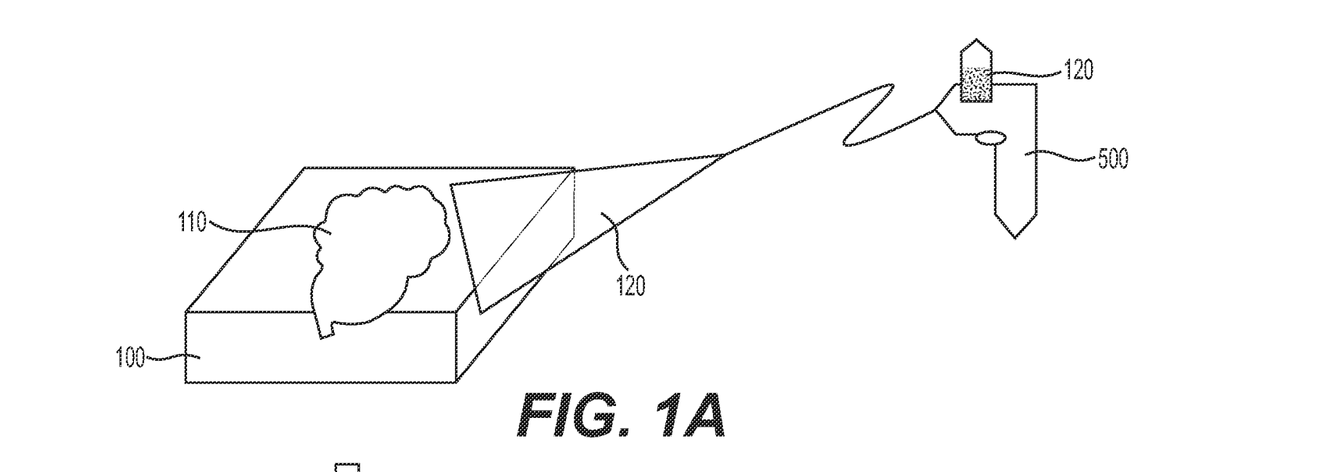
FIGS. 1A-1C illustrate an exemplary method of treatment, in accordance with some aspects of the present disclosure.
Figure 1B:
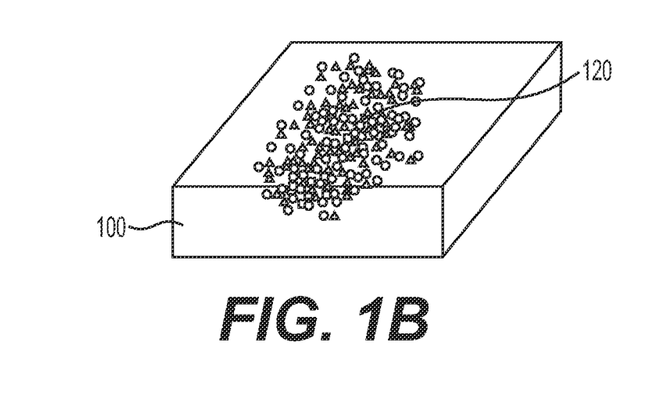

In FIG. 1A, a composition 120 may be applied to target site 110 via medical device 500, e.g., a catheter. In this example, composition 120 comprises a hemostatic agent and a pH agent, wherein both are in particle form or both are in liquid form. For example, hemostatic agent particles (e.g., particles comprising a chitosan salt and/or chitosan cross-linked with TPP) and pH agent particles (e.g., sodium bicarbonate particles) may be combined to form the composition 120 and optionally stored prior to application to target site 110.

Figure 1C:
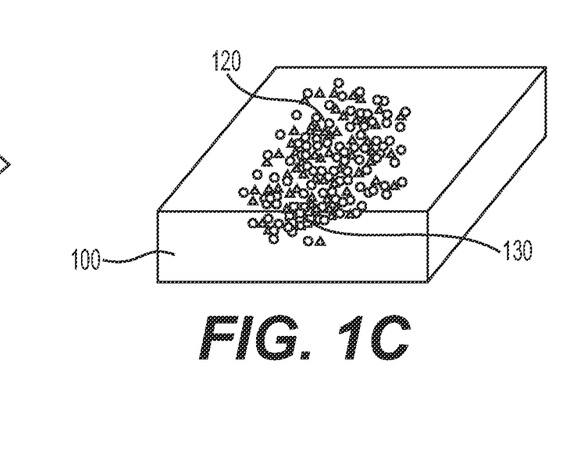

Once the composition 120 is applied, an initial barrier, e.g., a physical barrier, may form over the tissue (see FIG. 1B) to initiate acute hemostasis. As discussed above, the hemostatic agent may function to absorb water from blood plasma and aggregate blood components, e.g., red blood cells, platelets, and/or blood proteins, to form a pseudoclot. In some cases, the hemostatic agent may increase the pH at and around target site 110 as discussed above. Simultaneously, the pH agent may increase the pH at and around target site 110 towards a neutral pH, e.g., a pH of about 7, to promote coagulation. Upon application of the composition 120, the pH agent and/or hemostatic agent present in the composition 120 may start working within seconds to neutralize stomach acid at target site 110 and within the immediate radius of target site 110. The pH agent and/or hemostatic agent may maintain a neutralized effect to target site 110 and its surrounding region for an amount of time, for example, about 10 minutes to about 1 hour, e.g., about 15 minutes to about 45 minutes, or about 30 minutes. Within this time frame, a platelet plug and fibrin clot 130 may form at target site 110 to promote sustained hemostasis, as shown in FIG. 1C. Once fibrin clot 130 forms, the tissue healing process may continue and at least a portion of the composition 120 may dissolve and/or be absorbed by the body over time.

In some examples, one or more pH agents may be applied to target site 110 before or after application of one or more hemostatic agents, wherein the hemostatic agent(s) may be applied alone or with the same or different pH agent(s). For example, the composition 120 of FIGS. 1A-1C may be a first composition, and a second composition comprising at least one pH agent that is the same or a different pH agent from the first composition 120 may be applied after applying the first composition 120. Application of the additional pH agent(s) may help to strengthen or create an additional barrier or mask to neutralize the pH at and around target site 110. The second composition may be applied anytime after the application of the first composition 120. For example, the second composition may be applied within seconds to minutes of applying the first composition 120, e.g., within about 10 minutes, about 5 minutes, about 1 minute, about 30 seconds, or about 5 seconds, e.g., from 1 second to 10 minutes, from 5 seconds to 5 minutes, or from 10 seconds to 30 seconds. Once fibrin clot 130 forms, the tissue healing process may continue, at least a portion of the first and second compositions may dissolve and/or be absorbed by the body over time to promote sustained hemostasis. The first and second compositions may be applied using the same medical device 500 (e.g., using the same or different lumens of medical device 500) or may be applied using different medical devices. For example, the first composition may be applied with a different medical device than the second composition, wherein the first and second compositions may be applied simultaneously and/or in sequence.

Figures 2A, 2B, 2C:
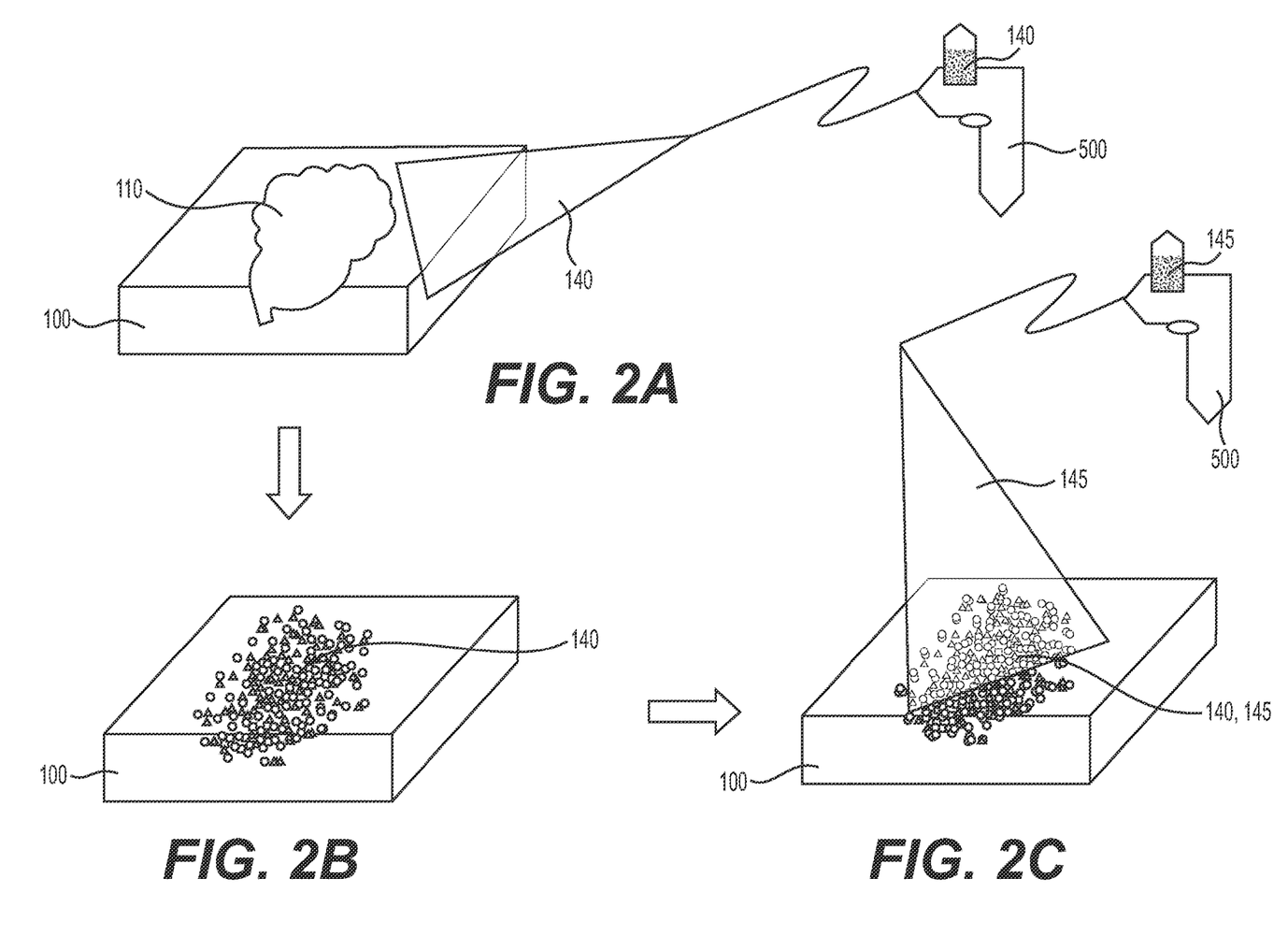
FIGS. 2A-2C illustrate another exemplary method of treatment, in accordance with some aspects of the present disclosure.

FIGS. 2A-2C illustrate another exemplary method wherein the hemostatic agent(s) and pH agent(s) are applied separately, sequentially, to target site 110. A first composition 140 comprising one or more hemostatic agents (without pH agents) may be applied to target site 110 first via medical device 500 as shown in FIG. 2A. Shortly after or immediately after formation of an initial barrier over the target site, as shown in FIG. 2B, a second composition 145 comprising one or more pH agents (without hemostatic agents) may be applied as shown in FIG. 2C. Each of the first composition 140 and the second composition 145 may be in particle or liquid form. For example, first composition 140 may comprise a hemostatic agent in particle form, such as a chitosan salt and/or chitosan cross-linked with TPP in particle form, and second composition 145 may comprise a pH agent such as sodium bicarbonate in particle form or formulated as a liquid solution. Applying the hemostatic agent first may provide for acute hemostasis (and optionally a localized neutralizing effect, such as in the case of chitosan cross-linked with TPP), and applying the pH agent afterward may help to neutralize the acidic environment of target site 110 to help stabilize and/or prolong the lifetime of fibrin clots formed at and around target site 110. Similar to the example of FIGS. 1A-1C, the second composition 145 may be applied any time after the application of the first composition 140. For example, the second composition 145 may be applied within seconds to minutes of applying the first composition 140, e.g., within about 10 minutes, about 5 minutes, about 1 minute, about 30 seconds, or about 5 seconds, e.g., from 1 second to 10 minutes, from 5 seconds to 5 minutes, or from 10 seconds to 30 seconds. Once fibrin clot 130 forms, the tissue healing process may continue, at least a portion of the first and second compositions may dissolve and/or be absorbed by the body over time to promote sustained hemostasis. The first and second compositions 140, 145 may be applied using the same medical device 500 (e.g., using the same or different lumens of medical device 500) or may be applied using different medical devices. Without wishing to be bound by theory, it is believed that applying the hemostatic agent(s) and the pH agent(s) separately may provide one or more benefits, such as reducing the risk of the pH agent(s) interfering with the activity of the hemostatic agent(s), e.g., the pH agent(s) negatively impacting initial acute hemostasis.

In other examples, first composition 140 may comprise one or more pH agents (without hemostatic agents) and second composition 145 may comprise one or more hemostatic agents (without pH agents). For example, to eliminate chalky residue that may result from powders, e.g., particles of sodium bicarbonate, the pH agent may be applied to target site 110 first, in liquid form, e.g., as a spray, followed by application of particles comprising chitosan, such as particles of a chitosan salt and/or particles of chitosan cross-linked with TPP.

According to some examples herein, a monomer and/or polymer may be applied to the tissue in addition to one or more hemostatic agents and one or more pH agents. The monomer/polymer may promote tissue healing by forming a patch at the target site. Thus, for example, the monomer may polymerize or the polymer may crosslink at and/or around the target site to form an additional barrier that protects the hemostatic agent(s) from degradation in the gastrointestinal environment. Such monomers/polymers may be formulated as a liquid, e.g., a solution, for application to the target site. In other examples, the monomers/polymers may be formulated as a powder for application to the target site. Exemplary monomers/polymers useful for the present disclosure include, but are not limited to, hydrogels, oleogels, and mixtures thereof. According to some aspects of the present disclosure, the monomers/polymers may be chosen from polyethylene glycol, polyethylene oxide, poloxamer, polyoxamine, polyvinyl alcohol, poly(lactic-co-glycolic acid, polyglycolic acid, polylactic acid, polycaprolactone, poly(L-glutamic acid), polyanhydrides, poly(N-isopropylacrylamide), polyaniline, or combinations thereof. Additionally or alternatively, the monomer/polymer(s) ma comprise alginate, e.g., sodium alginate, and/or one or more cellulose polymers such as hydroxypropylmethylcellulose, methyl cellulose, ethyl cellulose, hydroxylpropylcellulose, hydroxyethylcellulose, and carboxymethylcellulose. In some examples, the monomers/polymers may include functional groups suitable for cross-linking with the hemostatic agent(s). For example, the monomers/polymers may comprise functional groups suitable for cross-linking with amine groups and/or other groups of chitosan. Exemplary functional groups include, e.g., esters and aldehydes, including, for example, N-hydroxysuccinimide (NHS) esters.

Optionally, the pH agent(s) may be encapsulated by one or more monomers/polymers, such as the monomers/polymers listed above. In at least one example, the hemostatic agent(s) in powder form and the pH agent(s) encapsulated in one or more monomers/polymers also in powder form may be applied to a target site (e.g., target site 110) simultaneously or consecutively. Then, a liquid of a desired pH may be applied to the hemostatic agent(s) and encapsulated pH agent to solubilize the materials at the target site and promote formation of a protective barrier over the target site, e.g., via a reaction such as cross-linking of complementary functional groups.

Figures 3A, 3B, 3C, 3D, 3E:
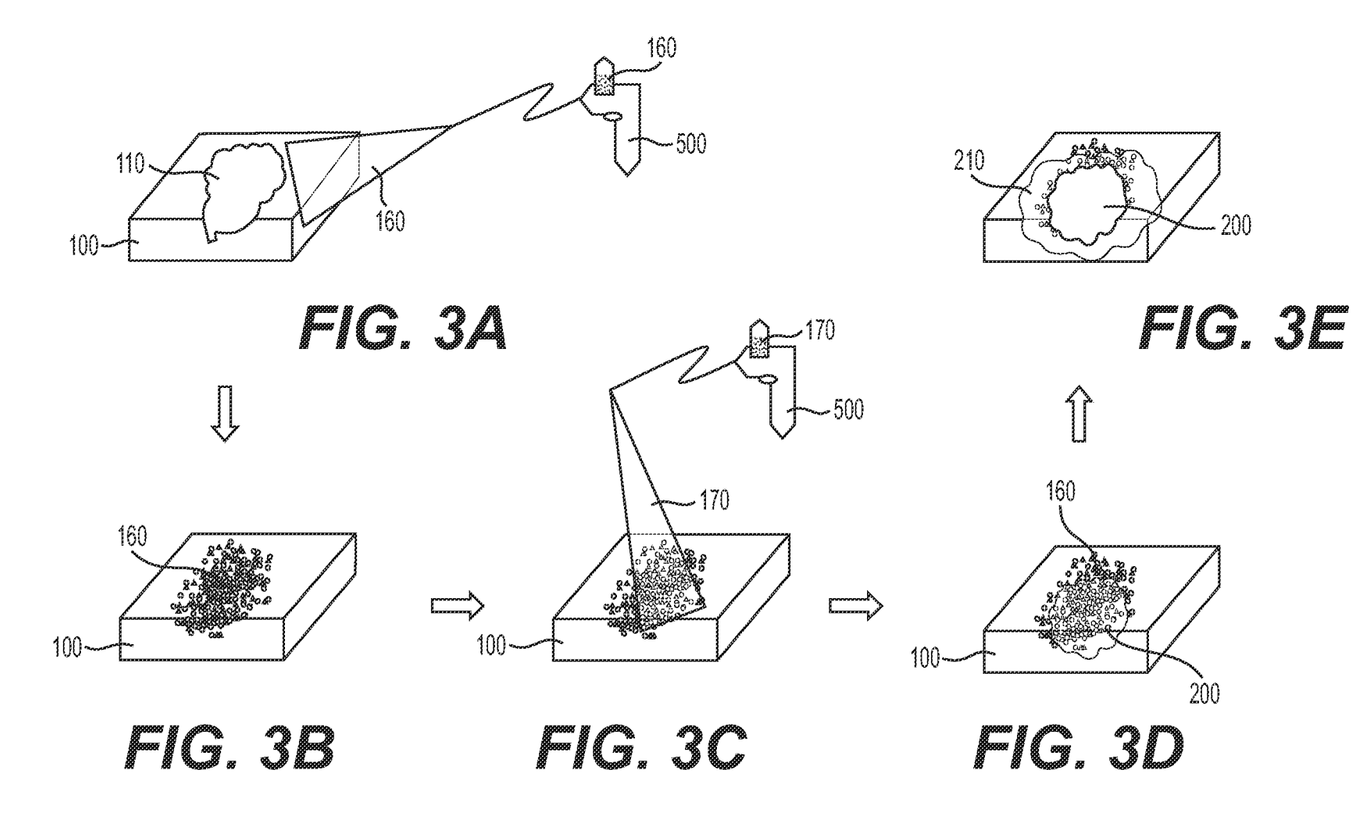
FIGS. 3A-3E illustrate another exemplary method of treatment, in accordance with some aspects of the present disclosure.

One such example that includes application of a monomer/polymer is depicted in FIGS. 3A-3E. In this example, a first composition 160 that comprises a combination of at least one hemostatic agent and at least one pH agent is applied to the target site 110 first via medical device 500 as shown in FIG. 3A. The first composition 160 may be in particle form or in liquid form. Once an initial barrier forms over the target site 110 as shown in FIG. 3B, a second composition 170 comprising a monomer and/or a polymer may be applied as shown in FIG. 3C. Thereafter, the monomer or polymer present in the second composition 170 may polymerize (in the case of a monomer) or crosslink (in the case of a polymer) to form a patch 200 over the applied hemostatic and pH agents of the first composition 160 and over target site 110 as shown in FIG. 3D.

The second composition 170 may further comprise one or more other compounds, for example, a pH agent and/or therapeutic or pharmaceutical agent. In at least one example, the second composition 170 comprises a pharmaceutical agent that decreases acid production in the stomach. For example, the second composition 170 may comprise a histamine-2 blocker such as famotidine. Such pharmaceutical agents may provide for a prolonged pH effect that helps to neutralize acidic conditions in the stomach to maintain a suitable environment for the patient's long term healing process.

The monomer or polymer may be applied within seconds/minutes of the application of the first composition 160. For example, the second composition 170 may be applied within seconds to minutes of applying the first composition 160, e.g., within about 10 minutes, about 5 minutes, about 1 minute, about 30 seconds, or about 5 seconds, e.g., from 1 second to 10 minutes, from 5 seconds to 5 minutes, or from 10 seconds to 30 seconds.

As mentioned above in reference to FIG. 3D, patch 200 may cover target site 110, allowing a fibrin clot to form. During and/or after formation of a fibrin clot, patch 200 may release a therapeutic or pharmaceutical agent present in the second composition 170 to target site 110 to produce and maintains a non-acid producing zone 210 as shown in FIG. 3E. Non-acid producing zone 210 may allow for long term control of the pH at and around target site 110. Once a fibrin clot forms, the tissue healing process may continue, at least a portion of the first and second compositions 160, 170 may dissolve and/or be absorbed by the body over time, and sustained hemostasis may be achieved.

Hemostatic systems comprising the compositions herein may help to stop, reduce, inhibit, and/or prevent bleeding at a target site for a period of time ranging from hours to days to weeks, e.g., a sufficient amount of time to allow the tissue to heal. In some cases, the target site may heal with a single application of hemostatic agent(s) and pH agent(s). In some cases, the target site may rebleed, in which case one or more additional applications of hemostatic agent(s), optionally in combination or sequentially with one or more pH agents, may be applied. For example, any of the methods discussed above and/or illustrated in FIG. 1A-1C, 2A-2C, or 3A-3E may be repeated. Further, for example, a medical professional may check for rebleeding periodically. If rebleeding has occurred, additional compositions (e.g., comprising hemostatic agent(s), pH agent(s), and/or monomers/polymers may be applied to the target site.

The compositions and methods herein may be part of a treatment regime. For example, once a patient is treated with the materials herein in an endoscopic procedure, the patient may be advised to take one or more medications to assist in reducing the production of stomach acid. For example, the patient may be advised to take an antacid orally at prescribed intervals.

Other embodiments of the present disclosure will be apparent to those skilled in the art from consideration of the specification and practice of the embodiments disclosed herein. It is intended that the specification and examples be considered as exemplary only, with a true scope and spirit of the present disclosure being indicated by the following claims.

What is claimed is:

1. A method of treating a patient, the method comprising:
introducing a medical device into a gastrointestinal system of a patient;
applying a first composition to a target site of the patient with the medical device, the first composition being in powder form and consisting of at least one hemostatic agent in powder form, wherein the target site includes bleeding stomach tissue; and
applying a second composition comprising at least one pH agent in powder form to the target site from 10 seconds to 30 seconds after applying the first composition to increase a pH of the target site;
wherein the at least one hemostatic agent reduces bleeding of the stomach tissue.

2. The method of claim 1, wherein the at least one pH agent comprises sodium bicarbonate, aluminum hydroxide, calcium hydroxide, magnesium hydroxide, bismuth subsalicylate, or a combination thereof.

3. The method of claim 1, wherein the at least one hemostatic agent comprises chitosan.

4. The method of claim 1, wherein the at least one hemostatic agent comprises chitosan cross-linked with tripolyphosphate, a chitosan salt, or a mixture thereof.

5. The method of claim 1, further comprising applying a therapeutic agent or a pharmaceutical agent after applying the first composition consisting of the at least one hemostatic agent and the second composition comprising the at least one pH agent.

6. The method of claim 5, wherein the method comprises applying the pharmaceutical agent, and the pharmaceutical agent comprises a histamine-2 blocker.

7. The method of claim 1, wherein the second composition is applied to the target site from 15 seconds to 20 seconds after applying the first composition to the target site.

8. A method of treating a patient, the method comprising:
applying a composition to a target site of a gastrointestinal system of the patient, the composition being in powder form and consisting of:
a hemostatic agent comprising a chitosan salt, chitosan cross-linked with tripolyphosphate, or a mixture thereof; and
at least one pH agent chosen from sodium bicarbonate, aluminum hydroxide, calcium hydroxide, magnesium hydroxide, bismuth subsalicylate, and combinations thereof;
wherein a weight ratio of the hemostatic agent to the pH agent (hemostatic agent:pH agent) ranges from 10:1 to 6:1;
wherein the target site includes bleeding stomach tissue; and
wherein the composition reduces bleeding of the stomach tissue.

9. The method of claim 8, wherein the composition is a first composition, and the method further comprises applying a second composition to the target site after applying the first composition, the second composition comprising at least one pH agent that is the same or different than the at least one pH agent of the first composition.

10. The method of claim 9, wherein the second composition is applied from 1 second to 30 seconds after applying the first composition.

11. The method of claim 8, wherein the composition is a first composition, and the method further comprises applying a second composition to the target site after applying the first composition, the second composition comprising a therapeutic agent or a pharmaceutical agent.

12. The method of claim 11, wherein the second composition comprises a histamine-2 blocker.

13. A method of treating a patient, the method comprising:
applying a first composition to a target site of a gastrointestinal system of the patient, the first composition being in powder form and consisting of:
a hemostatic agent comprising chitosan cross-linked with tripolyphosphate; and
at least one pH agent chosen from sodium bicarbonate, aluminum hydroxide, calcium hydroxide, magnesium hydroxide, bismuth subsalicylate, or combinations thereof; and
applying a second composition to the target site after applying the first composition, the second composition comprising at least one pH agent that is the same or different than the at least one pH agent of the first composition;
wherein the target site includes bleeding tissue;
wherein a weight ratio of the hemostatic agent to the pH agent (hemostatic agent:pH agent) in the first composition ranges from 10:1 to 1:10; and
wherein the first composition reduces bleeding of the tissue.

14. The method of claim 13, wherein the second composition is applied to the target site from 10 seconds to 30 seconds after applying the first composition to the target site.

15. The method of claim 14, wherein the second composition is applied to the target site from 15 seconds to 20 seconds after applying the first composition to the target site.

16. The method of claim 13, wherein the first composition has an average particle diameter of about 100 μm to about 750 μm.

* * * * *